United States Patent [19]

Whelan, III

[11] 4,304,011
[45] Dec. 8, 1981

[54] SEMI-CONSTRAINED METACARPOPHALANGEAL PROSTHESIS

[76] Inventor: Edward J. Whelan, III, 5 Sandy Point Rd., Savannah, Ga. 31404

[21] Appl. No.: 181,239

[22] Filed: Aug. 25, 1980

[51] Int. Cl.³ .................................................. A61F 1/24
[52] U.S. Cl. ..................................... 3/1.91; 128/92 C
[58] Field of Search ............................... 3/1.9–1.913; 128/92 C, 92 CA

[56] References Cited

U.S. PATENT DOCUMENTS

| | | | |
|---|---|---|---|
| 3,506,982 | 4/1970 | Steffee | 3/1.91 |
| 3,760,427 | 9/1973 | Schultz | 3/1.91 |
| 3,805,302 | 4/1974 | Mathys | 3/1.91 |
| 3,893,196 | 7/1975 | Hochman | 3/1.91 |
| 3,938,198 | 2/1976 | Kahn et al. | 3/1.912 |
| 3,939,496 | 2/1976 | Ling et al. | 3/1.91 |
| 4,059,854 | 11/1977 | Laure | 3/1.91 |
| 4,106,128 | 8/1978 | Greenwald et al. | 3/1.91 |
| 4,158,893 | 6/1979 | Swanson | 3/1.91 |
| 4,172,296 | 10/1979 | D'Errico | 3/1.91 X |

Primary Examiner—Ronald L. Frinks
Attorney, Agent, or Firm—Nathaniel A. Humphries

[57] ABSTRACT

A metacarpophalangeal joint prosthesis includes a proximal component and a distal component mounted for relative pivotal movement with each including a metal core mounted in a plastic capsule with the proximal metal core having a cup-like socket in which a plastic bearing cup is positioned to receive a spherical pivot ball on the distal metal core member. A guide slot extends through the plastic bearing cup and the cup-like socket to guide the distal metal core member when said distal core member is in a pivoted flexion position with respect to the proximal core member to prevent lateral pivotal movement of the distal component under such conditions while permitting such movement when the components are in linear extended relation in the manner of the natural joint.

15 Claims, 9 Drawing Figures

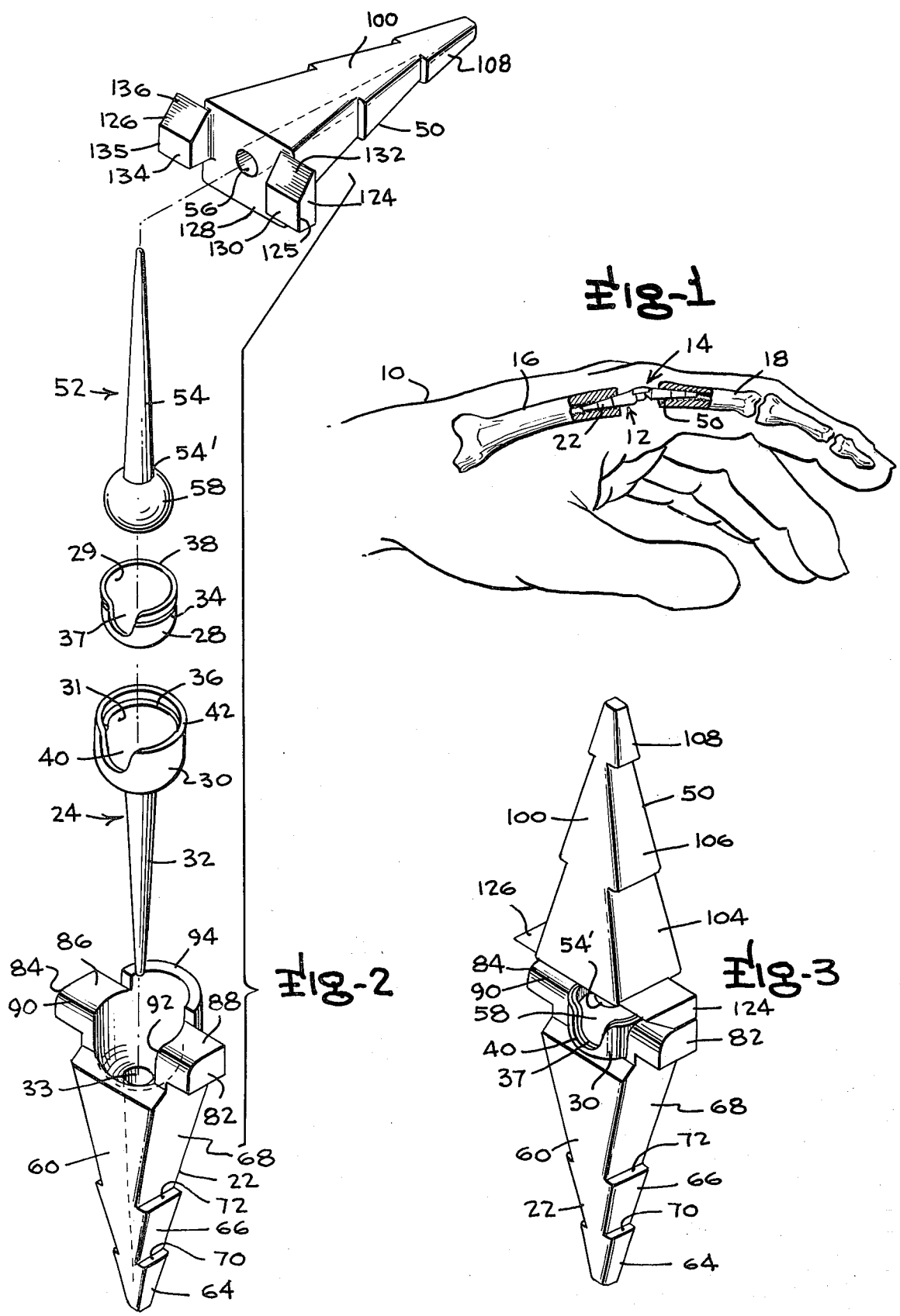

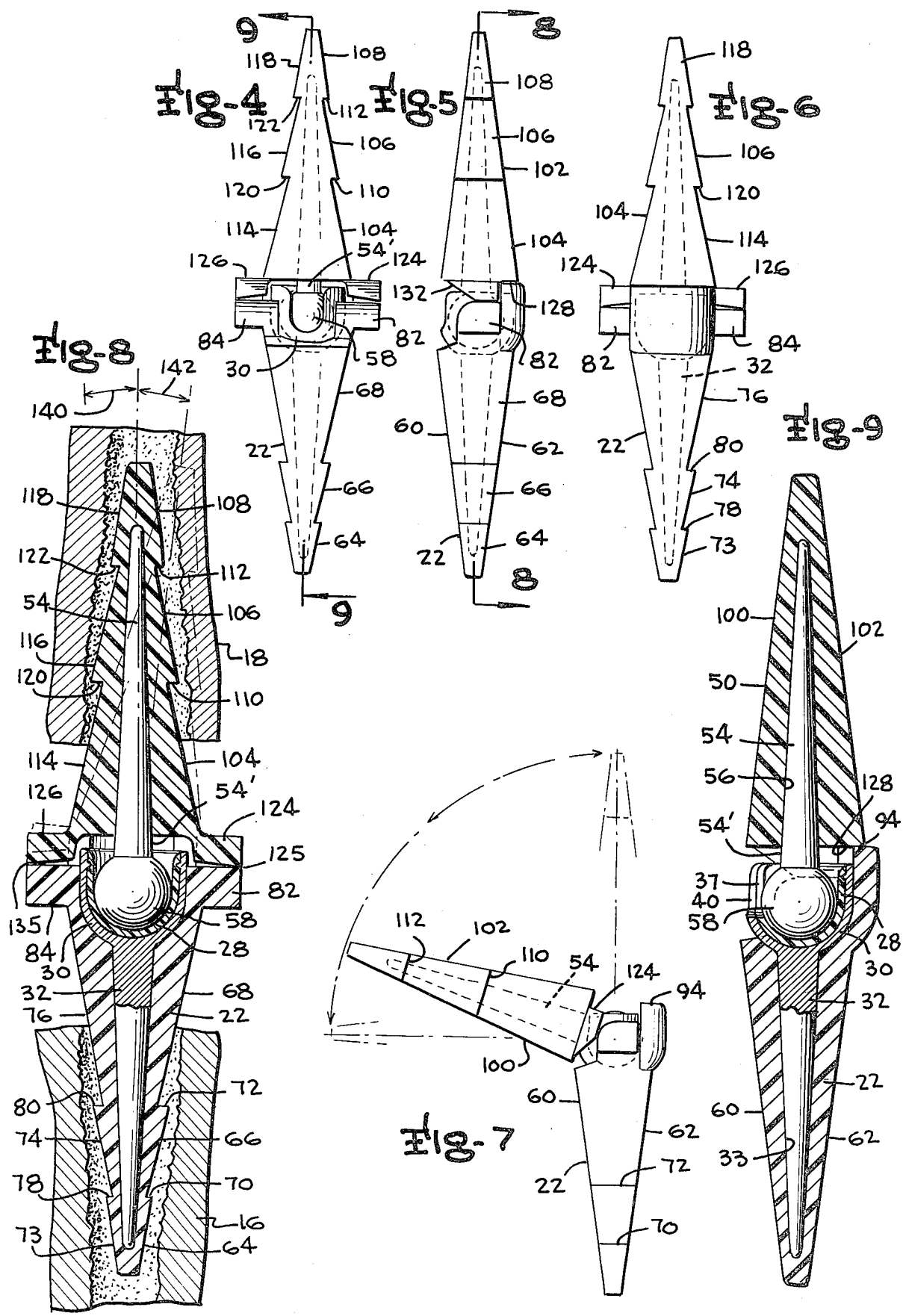

SEMI-CONSTRAINED METACARPOPHALANGEAL PROSTHESIS

BACKGROUND OF THE INVENTION

This invention is in the field of prostheses and is more particularly directed to a metacarpophalangeal prosthesis for replacement of the natural metacarpophalangeal joint.

Prior known prostheses for joint replacement have been provided in a variety of forms employing metal, plastic, silicone rubber and other components as evidenced by U.S. Pat. Nos. 3,462,765; 3,488,779; 3,506,982; 3,593,342; 3,760,427; 3,795,922; 3,805,302; 3,868,730; 3,893,196; 3,899,796; 3,906,550; 3,946,445; 3,978,528; 3,986,212; 3,990,116; 3,991,425; 4,011,603; 4,059,854; 4,065,817; 4,131,957; 4,146,936; 4,158,893 and 4,172,296.

While the prior known protheses have been beneficial in many ways, none have been able to duplicate the action of the natural metacarpophalangeal joint. Specifically, the natural joint does not merely provide a pivotal hinge function without any lateral motion but instead permits lateral motion when the joint is extended in linear manner but does not permit such motion when the joint is in a bent or flexed position such as when the distal and proximal components are in a generally perpendicular relationship. Consequently, duplication of the natural joint motion would require that any prosthesis allow for a full range of motion when the joint is in its extended linear condition while not allowing lateral motion when the joint is in its flexed or bent condition. No prior known prosthesis has been able to accomplish this result.

Therefore, it is the primary object of this invention to provide a new and improved prosthesis.

A more specific object of the present invention is the provision of a new and improved metacarpophalangeal prosthesis.

SUMMARY OF THE INVENTION

Achievement of the foregoing objects is enabled by the preferred embodiment of this invention by the provision of a prosthesis including a distal and a proximal component, each of which includes a stainless steel core including a tapered stem enclosed within a capsule formed of inert material such as silicone rubber. The outer surface of each capsule is defined by front and rear planar surfaces which converge toward the outer end of the capsule and by first and second sides defined by a series of parallel planar surfaces separated by transverse planar surfaces to provide a series of retaining steps having an appearance of a step-like array along the first and second sides of the capsule.

The distal core member of the distal component additionally includes a spherical pivotal ball on the inner end of the tapered stem while the inner end of the proximal metal core component consists of a cup-like socket member in which polyethylene cup is positioned with the interior of the polyethylene cup being spherical in shape and dimensioned to matingly receive the spherical pivot ball of the distal metal core member. The cup-like socket of the metal core component of the proximal component and the polyethylene cup are provided with aligned guide slots extending from their distal end inwardly of a width sufficient to permit the inner end of the stem of the distal metal core component to be received for movement during pivotal movement of the prosthesis to preclude lateral movement of the pin during such movement in the manner of the natural joint. However, when the distal metal core component is extending outwardly in general linear alignment with the proximal metal core component, the stem of the distal metal core component is completely clear of the slot so that it is capable of limited transverse or lateral pivotal movement to a certain extent in the same manner as the natural joint. The distal capsule and the proximal capsule include facing shoulder portions of generally planar configuration extending in planes perpendicular to the axis of the proximal component when the distal and proximal components are in their extended linearly aligned position. The shoulder components are of some flexibility so that limited pivotal lateral movement is consequently possible. Additionally, the proximal capsule includes first and second curved side surfaces which are faced, respectively, by the first and second shoulder portions of the distal capsule during pivotal movement of the distal component. The distal capsule shoulders have front surfaces oriented in a plane extending at approximately 45° with respect to the axis of the distal component so that during bending or pivoting movement of the distal component a clearance is provided to permit the shoulders of the distal component to move along the curved guide surfaces of the proximal capsule.

A better understanding of the nature and operation of the preferred embodiment will be achieved when the following detailed description is considered in conjunction with the appended drawings in which like reference numerals are used for the same parts as illustrated in the different figures.

BRIEF DESCRIPTION OF THE DRAWINGS

FIG. 1 is a perspective view with portions removed of the preferred embodiment as mounted in the human hand in replacement of the natural metacarpophalangeal joint;

FIG. 2 is an exploded perspective view of the preferred embodiment;

FIG. 3 is a perspective view of the preferred embodiment in assembled condition;

FIG. 4 is a front elevation view of the preferred embodiment;

FIG. 5 is a right side elevation view of the preferred embodiment;

FIG. 6 is a rear elevation view of the preferred embodiment;

FIG. 7 is a side elevation view of the preferred embodiment illustrating the components in a bent or pivoted condition;

FIG. 8 is a sectional view taken along lines 8—8 of FIG. 5; and

FIG. 9 is a sectional view taken along lines 9—9 of FIG. 4.

DESCRIPTION OF THE PREFERRED EMBODIMENT

Attention is initially invited to FIG. 1 of the drawings which illustrates a human hand 10 in which the preferred embodiment of the invention is positioned in place of the metacarpophalangeal joint with the preferred embodiment including a proximal component 12 and a distal component 14 which are respectively mounted in the ends of the medullary canals of the metacarpal bone 16 and the phalanx bone 18 of the index finger.

Proximal component 12 consists of a proximal capsule 22 formed of silicone rubber such as employed in Swanson U.S. Pat. No. 4,158,893 and a proximal core 24 formed of stainless steel alloy with the core being substantially enclosed within the proximal capsule 22. Proximal component 12 additionally includes a bearing cup 28 formed of polyethylene and received in a cup-like socket 30 unitarily attached to the larger end of the tapered stem 32 of the proximal metal core member 24. Stem 32 is received in mating axial cavity 33 of proximal capsule 22. The outer surface of the polyethylene bearing cup 28 is provided with a protruding retaining flange 34 which is matingly received in a groove 36 in the interior surface of the cup-like socket 30. The interaction of the retaining flange 34 and groove 36 serves to retain the bearing cup 28 in the cup-like socket 30. Additionally, adhesive can be employed for retaining the bearing cup 28 in the cup-like socket 30 if desired. A guide slot 37 extends proximally from the distal end 38 of the palmer surface of bearing cup 28 and a similar guide slot 40 extends proximally from the distal end 42 of the cup-like socket 30 with the guide slots 37 and 40 being in aligned relation in the assembled embodiment.

Distal component 14 of the preferred embodiment comprises a distal capsule 50 and a distal core member 52. Distal capsule 50 is formed of the same silicone rubber material as the proximal capsule 22 while the core member 52 is of the same stainless steel alloy as the proximal core member 24. Distal core member 52 includes a tapered stem 54 matingly received within cavity 56 of the distal capsule 50 with the larger end 54' of the distal core stem 54 being connected to a polished spherical pivot ball 58 which is of approximately 5 mm diameter and is dimensioned to be matingly received by the spherical inner surface 29 of the polyethylene bearing cup 28. Guide slots 37 and 40 are aligned and are of such a width as to easily permit the movement of the larger end portion 54' of stem 54 into the slots; however, the slots are dimensioned to prevent lateral pivotal movement of the stem 54 after it has moved into the slot during pivotal movement of the joint. Guide slot 40 is slightly wider than guide slot 37 so as to preclude metal-to-metal contact between surface 54' and bearing cup 28.

Proximal capsule 22 is formed of tapered palmar and dorsal planar surfaces 60 and 62, respectively, as best illustrated in FIGS. 2 and 5 with one of the sides of the capsule being defined by three parallel planar surfaces 64, 66 and 68 and two connecting transverse planar surfaces 70 and 72. The other side of the proximal capsule 22 is similarly defined by parallel planar surfaces 73, 74 and 76 connected by transverse planar surfaces 78 and 80 and in identical manner to the other side. It will therefore be apparent that the right and left sides of the proximal capsule are step-like in appearance and shape. Additionally, first and second positioning shoulders 82 and 84 are provided on opposite sides of the proximal capsule and respectively include upper surfaces 86 and 88 of planar configuration from the forward edges of which curved guide surfaces 90 and 92 extend. An accurate positioning abutment 94 is provided on the upper rear extent of the proximal capsule for engagement with surface 128 of the distal capsule limiting pivotal movement of the distal component in a clockwise direction beyond the position illustrated in FIG. 9.

Distal capsule 50 is similar to the proximal capsule 22 with the outer configuration being defined by a front or palmar tapered planar surface 100 and a rear or dorsal tapered planar surface 102 with a first side including parallel planar surfaces 104, 106 and 108 which are connected by transverse planar surfaces 110 and 112. In like manner, the opposite sides of the distal capsule includes parallel planar surfaces 114, 116 and 118 with surfaces 114 and 116 being connected by a transverse planar surface 120 and the surfaces 116 and 118 being connected by transverse planar surface 122. Distal capsule 50 also includes first and second shoulders 124 and 126 provided on opposite sides of surface 128. Shoulder 124 includes a planar proximal facing surface 130 and a canted front surface 132 which is oriented at approximately 45° with respect to the longitudinal axis of the distal component. Similarly, shoulder 126 includes a planar proximal facing surface 134 and a canted front surface 136.

When the distal component and the proximal component are in their aligned positions, as illustrated in FIGS. 4, 5, 6, 8 and 9, the surface 130 faces the surface 88 of shoulder 82 and the surface 134 faces the surface 86 of shoulder 84. However, only the outer edges 125 and 135 of shoulders 124 and 126 actually contact the surfaces 88 and 86 when the parts are in linear alignment as shown in FIG. 8. However, the shoulders 124 and 126 are formed of somewhat flexible material and can consequently bend to permit lateral pivotal deflection of approximately 15 degrees of hyperextension as shown by arrows 140 and 142, as shown in FIG. 8, so as to provide for lateral pivotal movement of the fingers in the manner of a natural joint. However, the shoulders 124 and 126 are of spring-like nature so that they provide a constant biasing force tending to return the distal component into aligned axial relationship with respect to the proximal component. The aforementioned pivotal lateral movement is not possible when the distal component is pivoted approximately 90° of flexion from its extended position of FIG. 9 to its position illustrated in FIG. 7, due to the fact that the base end surface 54' of stem 54 is closely received within the slots 37, 40 so as to be incapable of lateral pivotal movement. When the base end surface 54' is positioned in slots 37, 40, the only possible substantial movement of the distal component is about the pivot axis extending perpendicularly to the paper through the center of the pivot ball 58 as viewed in FIG. 7.

Rearward pivotal movement in counterclockwise direction of the distal component beyond the position illustrated in FIG. 5 is precluded by engagement of the surface 128 of the distal capsule with the positioning abutment 94 of the proximal capsule.

Thus, it will be seen that the preferred embodiment permits pivotal movement of the joint in exactly the same manner as the natural joint. The relatively soft nature of the proximal and the distal capsule precludes damage to the bone end in which they are conventionally retained by methyl methacrylate cement. Also, the low-friction contact between the stainless steel alloy surface of pivot ball 58 and the smooth inner surface 29 of bearing cup 28 results in a trouble-free and long-lasting prosthesis.

Numerous modifications of the preferred embodiment, which will not depart from the spirit and scope of the invention, will undoubtedly occur to those skilled in the art; and it should therefore be understood that the spirit and scope of the invention is to be limited solely by the appended claims.

I claim:

1. A prosthesis for joint replacement comprising a proximal component and a distal component mounted for relative pivotal movement, said proximal component including a proximal metal core member and including a tapered stem portion having a large end portion and a small end portion and a cup-like socket having a partial spherical internal surface and being connected to said large end portion, a plastic bearing cup matingly positioned in said cup-like socket and a proximal capsule formed of inert, non-metallic material enclosing said proximal metal core member, said distal component including a distal capsule formed of inert, non-metallic material, a distal metal core member including a tapered stem having a large end portion and a small end portion embedded in said distal capsule, a spherical pivot ball on said large end of said distal metal core member, said spherical pivot ball being matingly positioned in said plastic bearing cup, aligned guide slots in the palmar sides of said plastic bearing cup and said cup-like socket for receiving the larger end portion of said tapered stem of the distal metal core member when said distal metal core member is in a pivoted flexion position with respect to the proximal metal core member so as to limit and prevent lateral pivotal movement of the distal component under such conditions and aligned shoulder means on said distal capsule and said proximal capsule engageable with each other when the distal component is in linear alignment with the proximal component, said shoulder means being of sufficient flexibility to permit limited lateral pivotal movement of the distal component when the components are in the last-mentioned position.

2. The prosthesis of claim 1 wherein said aligned shoulder means comprise first and second proximal shoulders on opposite sides of the distal end of the proximal capsule and first and second distal shoulders on opposite sides of the proximal end of the distal capsule positioned respectively in alignment with said first and second proximal shoulders.

3. The prosthesis of claim 1 wherein said aligned shoulder means comprise first and second proximal shoulders on opposite sides of the distal end of the proximal capsule and first and second distal shoulders on opposite sides of the proximal end of the distal capsule and wherein said distal shoulders have outer edge portions on proximal facing surfaces and said proximal shoulders have distal facing surfaces which are opposed to said proximal facing surfaces wherein said proximal facing surfaces are canted downwardly so that their outer edge portions provide the only contact with said distal facing surfaces when said distal component is in linear alignment with said proximal component.

4. The prosthesis of claim 3 wherein said proximal capsule and distal capsule are formed of silicone rubber.

5. The prosthesis of claim 4 wherein said proximal core and distal core are formed of stainless steel alloy.

6. The prosthesis of claim 5 wherein said plastic bearing cup is formed of polyethylene.

7. The prosthesis of claim 1 wherein said guide slot in the palmar side of said cup-like socket is of slightly greater width than the guide slot of said plastic bearing cup so that said tapered stem of said distal core cannot contact the edges of the guide slot in the palmar side of the cup-like socket.

8. The prosthesis of claim 7 wherein said distal capsule and palmar capsule each include tapered palmar and dorsal planar surfaces and stepped side surfaces defined by a plurality of parallel planar surfaces and connecting transverse surfaces.

9. The prosthesis of claim 7 wherein said aligned shoulder means comprise first and second proximal shoulders on opposite sides of the distal end of the proximal capsule and first and second distal shoulders on opposite sides of the proximal end of the distal capsule and wherein said distal shoulders have outer edge portions on proximal facing surfaces and said proximal shoulders have distal facing surfaces which are opposed to said proximal facing surfaces wherein said proximal facing surfaces are canted downwardly so that their outer edge portions provide the only contact with said distal facing surfaces when said distal component is in linear alignment with said proximal component.

10. The prosthesis of claim 9 wherein said proximal capsule and distal capsule are formed of silicone rubber.

11. The prosthesis of claim 10 wherein said proximal core and distal core are formed of stainless steel alloy.

12. The prosthesis of claim 1 wherein said distal capsule and said palmer capsule each include tapered palmar and dorsal planar surfaces and stepped side surfaces including a plurality of parallel planar surfaces and connecting transverse planar surfaces and said shoulder means comprise first and second proximal shoulders on opposite sides of the distal end of the proximal capsule and first and second distal shoulders on opposite sides of the proximal end of the distal capsule and wherein said distal shoulders have outer edge portions on proximal facing surfaces and said proximal shoulders have distal facing surfaces which are opposed to said proximal facing surfaces wherein said proximal facing surfaces are canted downwardly so that their outer edge portions provide the only contact with said distal facing surfaces when said distal component is in linear alignment with said proximal component.

13. The prosthesis of claim 1 wherein said guide slot in the palmar side of said cup-like socket is of slightly greater width than the guide slot of said plastic bearing cup so that said tapered stem of said distal core cannot contact the edges of the guide slot in the palmar side of the cup-like socket, said distal capsule and palmar capsule are formed of silicone rubber and each include tapered palmar and dorsal planar surfaces and stepped side surfaces defined by a plurality of parallel planar surfaces and connecting transverse surfaces, said aligned shoulder means comprise first and second proximal shoulders on opposite sides of the distal end of the proximal capsule and first and second distal shoulders on opposite sides of the proximal end of the distal capsule and wherein said distal shoulders have outer edge portion proximal facing surfaces and said proximal shoulders have distal facing surfaces which are opposed to said proximal facing surfaces wherein said proximal facing surfaces are canted downwardly so that their outer edge portions provide the only contact with said distal facing surfaces when said distal component is in linear alignment with said proximal component.

14. The prosthesis of claim 13 wherein said proximal core and distal core are formed of stainless steel alloy.

15. The prosthesis of claim 14 wherein said plastic bearing cup is formed of polyethylene.